US006576677B1

(12) United States Patent
Ukai et al.

(10) Patent No.: US 6,576,677 B1
(45) Date of Patent: Jun. 10, 2003

(54) MEDICINAL COMPOSITIONS WITH RELIEVED BITTERNESS

(75) Inventors: Koji Ukai, Gifu (JP); Tsutomu Harada, Aichi (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/530,391

(22) PCT Filed: Aug. 26, 1999

(86) PCT No.: PCT/JP99/04616

§ 371 (c)(1),
(2), (4) Date: Apr. 28, 2000

(87) PCT Pub. No.: WO00/12135

PCT Pub. Date: Mar. 9, 2000

(30) Foreign Application Priority Data

Aug. 28, 1998 (JP) ............................................. 10-242997

(51) Int. Cl.[7] .......................... A61K 47/32; A61K 9/68; A61K 9/36; A61K 9/16
(52) U.S. Cl. .................... 514/772.4; 514/974; 514/963; 424/441; 424/480; 424/495; 424/489
(58) Field of Search .............................. 514/772.4, 974, 514/963; 424/441, 480, 495, 489

(56) References Cited

U.S. PATENT DOCUMENTS

| | | | | |
|---|---|---|---|---|
| 5,077,053 A | * | 12/1991 | Kuncewitch et al. | 424/441 |
| 5,084,278 A | * | 1/1992 | Mehta | 424/441 |
| 5,489,436 A | * | 2/1996 | Hoy et al. | 424/441 |
| 5,962,535 A | * | 10/1999 | Miyamoto et al. | 514/724 |

FOREIGN PATENT DOCUMENTS

| | | |
|---|---|---|
| JP | 60-204712 A | 10/1985 |
| JP | 60204712 A | 10/1985 |
| JP | 3-5418 A | 1/1991 |
| JP | 03005418 A | 1/1991 |
| JP | 03287535 A | 12/1991 |
| JP | 04018015 A | 1/1992 |
| JP | 9-143100 A | 6/1997 |
| JP | 09143100 A | 6/1997 |
| JP | 10-36292 A | 2/1998 |
| JP | 10036292 A | 2/1998 |
| JP | 411106353 | * 4/1999 |

* cited by examiner

Primary Examiner—Thurman K. Page
Assistant Examiner—Blessing Fubara
(74) Attorney, Agent, or Firm—Birch, Stewart, Kolasch & Birch, LLP

(57) ABSTRACT

The present invention provides a composition alleviated in a bitter taste or the like of a medicament. The present invention relates to a composition comprising a basic medicament having an unpleasant taste and polyvinylpyrrolidone and/or copolyvidone; or a method for alleviating an unpleasant taste of a basic medicament having the unpleasant taste by adding polyvinylpyrrolidone and/or copolyvidone. The present invention further provides a composition comprising (1) a basic medicament, (2) polyvinylpyrrolidone and/or copolyvidone, and (3) propylene glycol and/or D-sorbitol; a composition comprising (1) a basic medicament, (2) polyvinylpyrrolidone and/or copolyvidone, and (4) an antioxidant; and a composition comprising (1) a basic medicament, (2) polyvinylpyrrolidone and/or copolyvidone, and (5) a colorant or flavor containing a sulfuric acid or sulfurous acid group.

21 Claims, No Drawings

MEDICINAL COMPOSITIONS WITH RELIEVED BITTERNESS

This application is the national phase under 35 U.S.C. §371 of PCT International Application No. PCT/JP99/04616 which has an International filing date of Aug. 26, 1999, which designated the United States of America.

FIELD OF THE INVENTION

The present invention relates to a composition or a method for reducing an unpleasant taste of a basic medicament having the unpleasant taste. In addition, the present invention relates to a composition alleviated in the defect of a composition containing a basic medicament, or a method for alleviating the defect.

PRIOR ART

Since oral administration of a medicament having an unpleasant taste such as bitter taste or numbness puts a burden on a patient and lowers compliance, various devices have been made to improve the taste of the medicament. When the medicament is solid such as tablets or granules, a bitter taste or the like can be masked in a relatively easy manner, for example, by coating or incorporation of the medicament in the matrix. For liquids, it is the common practice to conceal a taste of the medicament under a sweet taste substance such as sucrose, which is however only a camouflage. A technique for essentially masking a bitter taste or the like is hardly known. Polyvinylpyrrolidone is known as a binder used for the preparation of tablets or the like. In JP-A 3-287535 and JP-A 4-18015, it is disclosed that a clear and stable aqueous solution is available by the addition of polyvinylpyrrolidone to a medicament sparingly soluble in water.

An object of the present invention is to alleviate an unpleasant taste of an oral medicament and moreover, to suppress the formation of a precipitate or decomposition product.

DISCLOSURE OF THE INVENTION

The present invention is directed to a composition comprising a basic medicament having an unpleasant taste and polyvinylpyrrolidone and/or copolyvidone. In addition, it is also directed to a method for alleviating an unpleasant taste of a basic medicament having the unpleasant taste by adding polyvinylpyrrolidone and/or copolyvidone thereto.

In a further aspect of the present invention, there is also provided a composition comprising (1) a basic medicament, (2) polyvinylpyrrolidone and/or copolyvidone, and (3) propylene glycol and/or D-sorbitol.

In a still further aspect of the present invention, there is also provided a composition comprising (1) a basic medicament, (2) polyvinylpyrrolidone and/or copolyvidone, and (4) an antioxidant.

In a still further aspect of the present invention, there is also provided a composition comprising (1) a basic medicament, (2) polyvinylpyrrolidone and/or copolyvidone, and (5) a colorant or flavor containing a sulfuric acid or sulfurous acid group.

The present invention makes it possible to reduce an unpleasant taste of a basic medicament having the unpleasant taste and this is the first object of the present invention.

Addition of polyvinylpyrrolidone and/or copolyvidone increases analogues to the basic medicament with the passage of time. The second object of the present invention is to suppress this increase of analogues.

Addition of a colorant or flavor having a sulfuric acid or sulfurous acid group happens to form an insoluble precipitate of the basic medicament. To suppress the formation of this precipitate is also an object of the present invention.

The basic medicament having an unpleasant taste in the present invention means a medicament in which a proton exists as a positive charge under acidic conditions and which has an unpleasant taste. Examples include ticlopidine hydrochloride, azelastine hydrochloride, etilefrine hydrochloride, diltiazem hydrochloride, propranolol hydrochloride, indeloxazine hydrochloride, aminoguanidine hydrochloride and donepezil hydrochloride. Among these, effects are particularly remarkable when donepezil hydrochloride is used. Donepezil hydrochloride is chemically named (1-benzyl-4-(5,6-dimethoxyindanon-2-yl) methylpiperidine hydrochloride, and it is a remedy for Alzheimer's disease of a slight to a medium degree. The aqueous solution thereof has a sharp bitterness and numbness.

In the present invention, polyvinylpyrrolidone and/or the like reduces an unpleasant taste. Described specifically, a basic medicament having an unpleasant taste, which the medicament has been positively charged by a proton bound thereto in a solution, is trapped by two pyrrolidone groups, whereby contact of the basic medicament with a taste bud is sterically hindered.

In the present invention, polyvinylpyrrolidone is a linear polymer of 1-vinyl-2-pyrrolidone and that having an average molecular weight ranging from several thousand to several million can be used, with that having an average molecular weight of about 10000 to 2000000 is preferable.

In the Japanese Pharmacopoeia, polyvinylpyrrolidones having an average molecular weight of 25000, 40000 and 1200000 are described as polyvinylpyrrolidone K25, polyvinylpyrrolidone K30 and polyvinylpyrrolidone K90, respectively. They are easily available as Kollidon, the trade name. In the codices of Japan, USA and England, it is officially described as povidone, while in the codex of Europe, it is officially described as polyvidone. Both are embraced in the present invention.

In the present invention, copolyvidone is a (6:4) copolymer of a chain-structured vinyl pyrrolidone and vinyl acetate and for example, it is officially described in the codex of Europe as copolyvidone. In the present invention, polyvinylpyrrolidone and copolyvidone may be used either singly or in combination.

In the present invention, a ratio of a basic medicament having an unpleasant taste to polyvinylpyrrolidone and/or copolyvidone differs depending on the molecular weight or the like and cannot be determined in the wholesale manner. Polyvinylpyrrolidone having an average molecular weight of 40000 is usually added in an amount of 5 to 200 parts by weight, preferably 20 to 200 parts by weight or 100 to 200 parts by weight, more preferably 140 to 200 parts by weight, each based on 1 part by weight of the basic medicament such as donepezil hydrochloride. It is added in an amount of 5 to 100 parts by weight for the solubilization of an insoluble substance, and 50 to 200 parts by weight for masking of a bitter taste. The larger the molecular weight of polyvinylpyrrolidone, the less the amount of it to be added, while the smaller, the more the amount to be added.

Specific examples of the formulated preparation usable in the present invention include water-soluble liquids, syrups, elixirs, jellies, dry syrups, effervescent preparations, lemonades, aerosols, ophthalmic solutions, nasal drops, suppositories, cataplasmas, liniments, lotions and fine granules. Among these, syrups and jellies are particularly preferable. Syrups are each available by adding a sweetener such as sucrose, glucose, mannitol, xylitol, aspartame, saccharin or sorbitol and optionally a taste and smell corrigent. Jellies are usually available by adding, to the composition of the present invention, a gum and then a sweetener such as sucrose, glucose, mannitol, xylitol, aspartame, saccharin or sorbitol and optionally a taste and smell corrigent. The pH of the preparation is usually in the range of from 3 to 7.

The composition of the present invention in the form of an aqueous solution can be produced by weighing necessary amounts of a medicament and polyvinylpyrrolidone and/or copolyvidone, adding a sweetener, flavor or the like as needed and then dissolving the resulting mixture in water. When the medicament is donepezil hydrochloride, the dose is usually 1 to 20 mg/once.

The present invention provides a composition containing a basic medicament. The basic medicament includes the above-mentioned basic medicament having an unpleasant taste and the other basic medicaments. Examples thereof include acebutolol hydrochloride, aprindine hydrochloride, alprenolol hydrochloride, ambroxol hydrochloride, isoprenaline hydrochloride, imipramine hydrochloride, diphenidol hydrochloride, diltiazem hydrochloride, thiamine hydrochloride, trazodone hydrochloride, bunazosin hydrochloride, bunitrolol hydrochloride, ranitidine hydrochloride and midodrine hydrochloride.

In addition, the present invention provides a composition comprising (1) a basic medicament, (2) polyvinylpyrrolidone and/or copolyvidone, and (3) propylene glycol and/or D-sorbitol, or a composition comprising (1) a basic medicament, (2) polyvinylpyrrolidone and/or copolyvidone, and (4) an antioxidant. When the basic medicament and polyvinylpyrrolidone and/or copolyvidone are mixed, an amount of analogues of the basic medicament happens to increase upon storage. Addition of propylene glycol and/or D-sorbitol, or an antioxidant, however, can markedly suppress the increase of the analogues. Accordingly, the present invention also provides a method for suppressing the formation of analogues by the addition of such substances. Examples of the antioxidant usable in the present invention include sodium bisulfite, sodium sulfite, sodium pyrosulfite, cysteine, citric acid, sodium edetate, ascorbic acid and erythorbic acid. They may be used either singly or in combination.

The present invention further provides a composition comprising (1) a basic medicament, (2) polyvinylpyrrolidone and/or copolyvidone, and (5) a colorant or flavor containing a sulfuric acid or sulfurous acid group. Although the addition, to a basic medicament, of a colorant or flavor containing a sulfuric acid or sulfurous acid group happens to form an insoluble precipitate, the addition of polyvinylpyrrolidone and/or copolyvidone can remarkably suppress the formation of the insoluble precipitate. Accordingly, the present invention also provides a method for suppressing the formation of an insoluble precipitate of the basic medicament caused by the addition of a colorant or flavor containing a sulfuric acid or sulfurous acid group, by the addition of polyvinylpyrrolidone and/or copolyvidone. Examples of the colorant or flavor containing a sulfuric acid or sulfurous acid group include Food Red No. 102 (trisodium 2-hydroxyazonaphthalene-4',6,8-trisulfonate), Food Red No. 40, Food Red No. 3 (2',4',5',7'-tetraiodofluorescein disodium salt), Food Red No. 2 (trisodium 2-hydroxyazonaphthalene-3,4',6-trisulfonate), Food Blue No. 1 (disodium 3-[N-ethyl-N-[4-[[-N-ethyl-N-(3-sulfonatobenzyl)amino]phenyl](2-sulfonatophenyl) methylene]-2,5-cyclohexadienyliden]ammoniomethyl] benzenesulfonate), Food Blue No. 2 (Acid Blue 74, disodium 2-(1,3-dihydro-3-oxo-5-sulfo-2H-indol-2-ylidene)-2,3-dihydro-3-oxo-1H-indole-5-sulfonate), Food Green No. 3 (disodium N-ethyl-N-[4-[[ethyl[(3-sulfophenyl)methyl]amino]phenyl](4-hydroxy-2-sulfophenyl)methylene]-2,5-cyclohexadien-1-ylidene]-3-sulfobenzenemethaneaminiumhydroxide), Food Yellow No. 4 (trisodium 3-carbonato-5-hydroxy-1-(4-sulfonatophenyl)-1H-pyrazol-4-azo-4'-(benzenesulfonate)) and Food Yellow No. 5 (disodium 2-hydroxy-6-sulfonatonaphthalen-1-azo-(4'-benzenesulfonate)). They may be used either singly or in combination.

The composition according to the present invention has remarkable effects for alleviating an unpleasant taste of a medicament and it is particularly useful when formulated into an orally administered liquid or jelly. It can remarkably suppress an increase, during storage, in the amount of the analogues of the basic medicament caused by the addition of polyvinylpyrrolidone and/or copolyvidone Moreover, it can prevent the formation of an insoluble precipitate of the basic medicament caused by the sulfuric acid or sulfurous acid group existing in the colorant or flavor.

The above-described effects will be described more specifically by Tests given below.

Test 1

Examinees A and B held in their mouths Test solution 1 having, dissolved therein, 5 mg of donepezil hydrochloride and 700 mg of polyvinylpyrrolidone (average molecular weight: about 40000) per 5 g of the solution and Control solution 1 having, dissolved therein, 5 mg of donepezil hydrochloride per 5 g of the solution, and then evaluated the degree of a bitter taste and numbness. The results are shown in Table 1. It is apparent from Table 1 that the composition according to the present invention remarkably alleviates an unpleasant taste of the medicament.

TABLE 1

| | A | | B | |
| --- | --- | --- | --- | --- |
| Examinee | Bitterness | Numbness | Bitterness | Numbness |
| Control solution 1 | +++ | +++ | +++ | +++ |
| Test solution 1 | | | | |
| just after the administration | ± | ± | ± | ± |
| 30 min after the administration | ± | + | ± | + |

Test 2

Seven healthy examinees held in their mouths test solutions (Test solution 2, 3 and 4) having, dissolved therein, 5 mg of donepezil hydrochloride and each of 700 mg, 500 mg and 100 mg of polyvinylpyrrolidone (average molecular weight: 40000) per 5 g of the solution and Control solution 2 having, dissolved therein, 5 mg of donepezil hydrochloride and 3 g of sorbitol per 5 g of the solution. Five seconds later, they disgorged each of the solutions, rinsed their mouths with tap water and evaluated the degree of a bitter taste and numbness. Evaluation was conducted when they took the solution (when the test solution or control solution was held in the mouth), just after disgorging (before rinsing with water) and 5 minutes after disgorging (after rinsing with water). The evaluation standards and results are shown in Table 2. From Table 2, it is evident that the more the amount of polyvinylpyrrolidone added, the scores relating to the bitter taste and numbness increased, that is, the effects for masking an unpleasant taste heightened. The effects for alleviating the numbness are particularly remarkable compared with the solution having sorbitol incorporated therein, suggesting that the effects of the present invention are not brought by false impression due to a sweet taste.

TABLE 2

Evaluation standards

| Evaluation scores | Bitterness | Numbness |
|---|---|---|
| 5 | No feeling | No feeling |
| 4 | Dim feeling | Dim feeling |
| 3 | Slightly bitter | Slightly numb |
| 2 | Bitter | Numb |
| 1 | Very bitter | Very numb |

Bitterness

| Examinee | Test solution 2 | Test solution 3 | Test solution 4 | Control solution 2 |
|---|---|---|---|---|
| K.U. | 5 | 4 | 2 | 4 |
| H.A. | 1 | 2 | 1 | 5 |
| T.H. | 3 | 2 | 2 | 5 |
| M.K. | 3 | 2 | 2 | 4 |
| S.I. | 3 | 2 | 2 | 3 |
| K.K. | 4 | 4 | 5 | 5 |
| Y.I. | 4 | 4 | 2 | 4 |
| Avg | 3.3 | 2.9 | 2.3 | 4.3 |

Numbness (when took the solution)

| Examinee | Test solution 2 | Test solution 3 | Test solution 4 | Control solution 2 |
|---|---|---|---|---|
| K.U. | 5 | 4 | 3 | 3 |
| H.A. | 5 | 5 | 4 | 5 |
| T.H. | 3 | 2 | 1 | 4 |
| M.K. | 5 | 3 | 3 | 3 |
| S.I. | 5 | 5 | 5 | 3 |
| K.K. | 5 | 5 | 5 | 5 |
| Y.I. | 5 | 4 | 3 | 4 |
| Avg | 4.7 | 4.0 | 3.4 | 3.9 |

Numbness (just after disgorging)

| Examinee | Test solution 2 | Test solution 3 | Test solution 4 | Control solution 2 |
|---|---|---|---|---|
| K.U. | 5 | 4 | 3 | 2 |
| H.A. | 5 | 5 | 3 | 5 |
| T.H. | 3 | 2 | 1 | 3 |
| M.K. | 5 | 5 | 4 | 2 |
| S.I. | 4 | 5 | 5 | 3 |
| K.K. | 5 | 5 | 5 | 5 |
| Y.I. | 4 | 3 | 3 | 4 |
| Avg | 4.4 | 4.1 | 3.4 | 3.4 |

Numbness (5 min after disgorging)

| Examinee | Test solution 2 | Test solution 3 | Test solution 4 | Control solution 2 |
|---|---|---|---|---|
| K.U. | 4 | 3 | 2 | 2 |
| H.A. | 5 | 4 | 2 | 5 |
| T.H. | 4 | 2 | 1 | 2 |
| M.K. | 5 | 5 | 4 | 3 |
| S.I. | 3 | 4 | 4 | 3 |
| K.K. | 5 | 5 | 4 | 5 |
| Y.I. | 4 | 3 | 3 | 4 |
| Avg | 4.3 | 3.7 | 2.9 | 3.4 |

Test 3

Samples obtained by incorporating 20% by weight of D-sorbitol into an aqueous solution containing 0.1% by weight of donepezil hydrochloride, obtained by incorporating 6% by weight of propylene glycol in the same aqueous solution and obtained by incorporating 5% by weight of polyvinylpyrrolidone to each of the above samples were stored at 60° C. for 2 weeks or 1 month and the amount of analogues to donepezil hydrochloride was measured. The results are shown in Table 3.

It is apparent from Table 3 that the formation of the analogues is remarkably suppressed by incorporating D-sorbitol or propylene glycol.

TABLE 3

Relationship between the amount of analogue and stabilizer

| | term of storage 60° C. | not incorporated (%) | D-sorbitol 20% incorporated (%) | propylene glycol 6% incorporated (%) |
|---|---|---|---|---|
| E2020 0.1% | 2 W | 0.00 | 0.00 | 0.00 |
| | 1 M | 0.03 | 0.00 | 0.00 |
| E2020 0.1% + | 2 W | 0.36 | 0.10 | 0.00 |
| PVP 5% | 1 M | 0.61 | 0.27 | 0.19 |

Test 4

Storage test was conducted by storing a preparation, which had been formulated as shown in Table 4, at 60° C. for 2 weeks or at 45° C. for 1 month. As a result, no analogues to donepezil hydrochloride was detected from the sample added with sodium bisulfite.

TABLE 4

| Fillers | Control mg/5 ml | Test sample mg/5 ml |
|---|---|---|
| Donepezil hydrochloride | 5 | 5 |
| Sodium bisulfite | | 1 |
| 70% D-sorbitol | 1785 | 1785 |
| Povidone K30 | 250 | 250 |
| Citric acid | 10 | 10 |
| Sodium citrate | proper amount | proper amount |
| Sodium benzoate | 5 | 5 |
| Food Red No. 40 | 0.05 | 0.05 |
| Strawberry flavor | 15 | 15 |
| Purified water | proper amount | proper amount |
| Total | 5 ml | 5 ml |
| Total amount of analogues (60° C./2W) | 0.60% | 0% |
| Total amount of analogues (45° C./1M) | 0.46% | 0% |

Test 5

From the formulation similar to that shown in Table 5 except that povidone is not added, a precipitate appeared under the storage conditions at a room temperature or in a cool place (4° C.).

TABLE 5

| Fillers | Prescription 1 mg/5 ml | Prescription 2 mg/5 ml |
|---|---|---|
| Donepezil hydrochloride | 5 | 5 |
| 70% D-sorbitol | 1785 | 1785 |
| Povidone K30 | 250 | 250 |
| Citric acid | 10 | 10 |
| Sodium citrate | proper amount | proper amount |
| Sodium benzoate | 5 | 5 |
| Food Red No. 40 | 0.05 | 0 |

TABLE 5-continued

| Fillers | Prescription 1 mg/5 ml | Prescription 2 mg/5 ml |
|---|---|---|
| Sunset Yellow | 0 | 0.02 |
| Strawberry flavor | 15 | 0 |
| Orange flavor | 0 | 15 |
| Purified water | proper amount | proper amount |
| Total | 5 ml | 5 ml |

EXAMPLES

The present invention will hereinafter be described more in detail in accordance with Examples, but the present invention should not be limited by them.

Example 1

A composition of the present invention was obtained by dissolving 50 mg of donepezil hydrochloride and 7.00 g of polyvinylpyrrolidone in 42.95 g of water.

Example 2

In 400 g of purified water were dissolved 500 mg of donepezil hydrochloride, 70 g of polyvinylpyrrolidone (average molecular weight: about 40000), 100 g of sorbitol, 1 g of saccharin sodium, 1 g of sodium citrate and 1.5 g of sodium benzoate, followed by the addition of citric acid to adjust the pH of the resulting solution to 5.0. The total volume of the solution was adjusted to 500ml, and 5 g portions of the solution were put into vials.

Example 3

Povidone (2.5 g, trade name: Kollidon 30) was added to purified water in portions to dissolve. A 70% D-sorbitol solution (17.9 g), 100 mg of citric acid (100 mg) and benzoic acid (50 mg) were added to the resulting solution to dissolve. Donepezil hydrochloride (50 mg) was then added to the resulting solution to dissolve, followed by the addition of sodium citrate to adjust the pH of the resulting solution to 3.9. To the resulting solution were further added 0.5 mg of Food Red No. 40 and 150 mg of strawberry flavor. Purified water was added to give a m total volume of 50 ml. Into vials were pipetted 5 ml portions of the resulting solution.

Example 4

Povidone (2.5 g, trade name: Kollidon 30) was added to purified water in portions to dissolve. A 70% D-sorbitol solution (17.9 g), 100 mg of citric acid (100 mg) and benzoic acid (50 mg) were added to the resulting solution to dissolve. Donepezil hydrochloride (50 mg) was then added to the resulting solution to dissolve, followed by the addition of sodium citrate to adjust the pH of the resulting solution to 3.9. To the resulting solution were further added 0.2 mg of Sunset Yellow and 150 mg of orange flavor, followed by the addition of purified water to give a total amount of 50 ml. Into vials were pipetted 5 ml portions of the resulting solution.

Example 5

Purified water was added to 50 mg of donepezil hydrochloride, 2.5 g of polyvinylpyrrolidone and 10 g of D-sorbitol to dissolve and the total volume was adjusted to 50 ml.

Example 6

Purified water was added to 50 mg of donepezil hydrochloride, 2.5 g of polyvinylpyrrolidone and 3 g of propylene glycol to dissolve and the total volume was adjusted to 50 ml.

Example 7

Povidone (2.5 g, trade name: Kollidon 30) was added to purified water in portions to dissolve. In the resulting solution, A 70% D-sorbitol solution (17.9 g), citric acid (100 mg), sodium benzoate (50 mg) and sodium bisulfite (10 mg) were added to the resulting solution to dissolve. Donepezil hydrochloride (5 mg) was added to the resulting solution to dissolve, followed by the addition of sodium citrate to adjust its pH to 3.9. To the resulting solution were further added Food Red No. 40 (0.5 mg) and 150 mg of strawberry flavor, followed by the addition of purified water to give a total amount of 50 ml. Into vials were pipetted 5 ml portions of the resulting solution.

Example 8

Povidone (2000 g, trade name: Kollidon 30) was added in portions to 15 L of purified water to dissolve. To the resulting solution was added 13280 g of a 70% D-sorbitol solution, followed by stirring for 30 minutes. After the complete dissolution of copolydone was confirmed, 400 g of a 20% citric acid solution and 400 g of a 10% sodium benzoate solution were added to the reaction mixture to dissolve. A solution of donepezil hydrochloride (40 g) 1dissolved in 1000 g of a 70% D-sorbitol solution was added thereto, followed by stirring. A solution of methylparaben (40 g) dissolved in 2400 g of propylene glycol was further added thereto, followed by stirring. A 10% sodium citrate solution was added to the resulting mixture to adjust the pH thereof to 3.9. To the resulting solution were further added a 0.2% solution (200 g) of Food Red No. 40 and 120 g of strawberry flavor, followed by the addition of purified water to give a total amount of 40 L. The resulting mixture was stirred. The resulting solution was filtered through a 0.22 $\mu$m filter and 5 ml portions were pipetted into aluminum stick packages.

What is claimed is:

1. A pharmaceutical composition comprising a medicament selected from the group consisting of ticlopidine hydrochloride, azelastine hydrochloride, etilefrine hydrochloride, diltiazem hydrochloride, propranolol hydrochloride, indeloxazine hydrochloride, aminoguanidine hydrochloride and donepezil hydrochloride and at least one component selected from the group consisting of polyvinylpyrrolidone and copolyvidone, said composition comprising 5 to 200 parts by weight of polyvinylpyrrolidone and/or copolyvidone per 1 part by weight of the medicament.

2. A method for alleviating an unpleasant taste of a medicament having the unpleasant taste selected from the group consisting of ticlopidine hydrochloride, azelastine hydrochloride, etilefrine hydrochloride, diltiazem hydrochloride, propranolol hydrochloride, indeloxazine hydrochloride, aminoguanidine hydrochloride and donepezil hydrochloride comprising adding thereto at least one component selected from the group consisting of polyvinylpyrrolidone and copolyvidone in an amount of from 5 to 200 parts by weight of polyvinylpyrrolidone and/or copolyvidone per 1 part by weight of the medicament.

3. The composition as claimed in claim 1, which is in the form of syrups, jellies, dry syrups, liquids, effervescent preparations, lemonades, elixirs, liniments or fine granules.

4. A composition comprising a medicament selected from the group consisting of ticlopidine hydrochloride, azelastine hydrochloride, etilefrine hydrochloride, diltiazem hydrochloride, propranolol hydrochloride, indeloxazine hydrochloride, aminoguanidine hydrochloride and donepezil hydrochloride, at least one component selected from the group consisting of polyvinylpyrrolidone and copolyvidone and at least one component selected from the group consisting of propylene glycol and D-sorbitol, said composition comprising 5 to 200 parts by weight of polyvinylpyrrolidone and/or copolyvidone per 1 part by weight of the medicament.

5. A method for suppressing the formation of analogues of a medicament selected from the group consisting of ticlopidine hydrochloride, azelastine hydrochloride, etilefrine hydrochloride, diltiazem hydrochloride, propranolol hydrochloride, indeloxazine hydrochloride, aminoguanidine hydrochloride and donepezil hydrochloride caused by the addition of polyvinylpyrrolidone or copolyvidone thereto, comprising further adding at least one component selected from propylene glycol and D-sorbitol, said polyvinylpyrrolidone and/or copolyvidone being added in an amount of from 5 to 200 parts by weight per 1 part by weight of the medicament.

6. A composition comprising a medicament selected from the group consisting of ticlopidine hydrochloride, azelastine hydrochloride, etilefrine hydrochloride, diltiazem hydrochloride, propranolol hydrochloride, indeloxazine hydrochloride, aminoguanidine hydrochloride and donepezil hydrochloride, at least one component selected from the group consisting of polyvinylpyrrolidone and copolyvidone, and an antioxidant, said composition comprising 5 to 200 parts by weight of polyvinylpyrrolidone and/or copolyvidone per 1 part by weight of the medicament.

7. The composition as claimed in claim 6, wherein the antioxidant is selected from the group consisting of sodium bisulfite, sodium sulfite, sodium pyrosulfite, cysteine, citric acid, sodium edetate, ascorbic acid and erythorbic acid.

8. A method for suppressing the formation of analogues of a medicament selected from the group consisting of ticlopidine hydrochloride, azelastine hydrochloride, etilefrine hydrochloride, diltiazem hydrochloride, propranolol hydrochloride, indeloxazine hydrochloride, aminoguanidine hydrochloride and donepezil hydrochloride caused by the addition of polyvinylpyrrolidone or copolyvidone thereto, comprising further adding an antioxidant, said polyvinylpyrrolidone and/or copolyvidone being added in an amount of from 5 to 200 parts by weight per 1 part by weight of the medicament.

9. A composition comprising a medicament selected from the group consisting of ticlopidine hydrochloride, azelastine hydrochloride, etilefrine hydrochloride, diltiazem hydrochloride, propranolol hydrochloride, indeloxazine hydrochloride, aminoguanidine hydrochloride and donepezil hydrochloride, at least one component selected from the group consisting of polyvinylpyrrolidone and copolyvidone, and a colorant or flavor containing a sulfuric acid or sulfurous acid group, said composition comprising 5 to 200 parts by weight of polyvinylpyrrolidone and/or copolyvidone per 1 part by weight of the medicament.

10. The composition as claimed in claim 9, wherein the colorant or flavor containing a sulfuric acid or sulfurous acid group is selected from the group consisting of trisodium 2-hydroxyazonaphthalene-4',6,8-trisulfonate, 2',4',5',7'-tetraiodofluorescein disodium salt, trisodium 2-hydroxyazonahthalene-3,4',6-trisulfonate, disodium 3-[N-ethyl-N-[4-[[-N-ethyl-N-(3-sulfonatobenzyl)amino]phenyl](2-sulfonatophenyl)methylene]-2,5-cyclohexadienyliden]ammoniomethyl]benzenesulfonate, disodium 2-(1,3-dihydro-3-oxo-5-sulfo-2H-indol-2-ylidene)-2,3-dihydro-3-oxo-1H-indole-5-sulfonate, disodium N-ethyl-N-[4-[[ethyl[(3-sulfophenyl)methyl]amino]phenyl](4-hydroxyl-2-sulfophenyl)methylene)-2,5-cyclohexadien-1-ylidene]-3-sulfobenzenemethaneaminiumhydroxide, trisodium 3-carbonato-5-hydroxy-1-(4-sulfonatophenyl)-1H-pyrazol-4-azo-4'-(benzenesulfonate) and disodium 2-hydroxy-6-sulfonatonaphthalen-1-azo-(4'-benzenesulfonate).

11. A method for suppressing the formation of an insoluble precipitate of a medicament selected from the group consisting of ticlopidine hydrochloride, azelastine hydrochloride, etilefrine hydrochloride, diltiazem hydrochloride, propranolol hydrochloride, indeloxazine hydrochloride, aminoguanidine hydrochloride and donepezil hydrochloride caused by the addition of a colorant or flavor containing a sulfuric acid or sulfurous acid group thereto, comprising adding at least one component selected from the group consisting of polyvinylpyrrolidone and copolyvidone in an amount of from 5 to 200 parts by weight per 1 part by weight of the medicament.

12. The composition as claimed in claim 1, wherein the medicament is donepezil hydrochloride.

13. A method for alleviating an unpleasant taste of a medicament in a pharmaceutical composition, said medicament selected from the group consisting of ticlopidine hydrochloride, azelastine hydrochloride, etilefrine hydrochloride, diltiazem hydrochloride, propranolol hydrochloride, indeloxazine hydrochloride, aminoguanidine hydrochloride and donepezil hydrochloride comprising adding thereto at least one component selected from the group consisting of polyvinylpyrrolidone and copolyvidone, said composition being in the form of syrups, jellies, dry syrups, liquids, effervescent preparations, lemonades, elixirs, liniments or fine granules, said polyvinylpyrrolidone and/or copolyvidone being added in an amount of from 5 to 200 parts by weight per 1 part by weight of the medicament.

14. The method of claim 5, wherein said medicament is in the form of syrups, jellies, dry syrups, liquids, effervescent preparations, lemonades, elixirs, liniments or fine granules.

15. The method of claim 8, wherein said medicament is in the form of syrups, jellies, dry syrups, liquids, effervescent preparations, lemonades, elixirs, liniments or fine granules.

16. The method of claim 11, wherein said medicament is in the form of syrups, jellies, dry syrups, liquids, effervescent preparations, lemonades, elixirs, liniments or fine granules.

17. The method of claim 11, wherein said colorant is selected from the group consisting of trisodium 2-hydroxyazonaphthalene-4',6,8-trisulfonate, 2',4',5',7'-tetraiodofluorescein disodium salt, trisodium 2-hydroxyazonahthalene-3,4',6-trisulfonate, disodium 3-[N-ethyl-N-[4-[[-N-ethyl-N-(3-sulfonatobenzyl)amino]phenyl](2-sulfonatophenyl)methylene]-2,5-cyclohexadienyliden]ammoniomethyl]benzenesulfonate, disodium 2-(1,3-dihydro-3-oxo-5-sulfo-2H-indol-2-ylidene)-2,3-dihydro-3-oxo-1H-indole-5-sulfonate, disodium N-ethyl-N-[4-[[ethyl[(3-sulfophenyl)methyl]amino]phenyl](4'-hydroxyl-2-sulfophenyl)methylene)-2,5-cyclohexadien-1-ylidene]-3-sulfobenzenemethaneaminiumhydroxide, trisodium 3-carbonato-5-hydroxy-1-(4-sulfonatophenyl)-1H-pyrazol-4-azo-4'-(benzenesulfonate) and disodium 2-hydroxy-6-sulfonatonaphthalen-1-azo-(4'-benzenesulfonate).

18. The method of claim 8, wherein said antioxidant is selected from the group consisting of sodium bisulfite, sodium sulfite, sodium pyrosulfite, cysteine, citric acid, sodium edetate, ascorbic acid and erythorbic acid.

19. The method as claimed in claim 11, further comprising adding at least one component selected from propylene glycol and D-sorbitol.

20. The method as claimed in claim 11, further comprising adding a colorant or flavor containing a sulfuric acid or sulfurous acid group.

21. The method as claimed in claim 11, further comprising adding an antioxidant.

* * * * *